United States Patent
Garault et al.

(10) Patent No.: US 7,981,657 B2
(45) Date of Patent: Jul. 19, 2011

(54) METHOD FOR OBTAINING VARIANTS OF LACTIC ACID BACTERIA USABLE FOR PRODUCING VITAMIN K2 AND APPLICATION TO THE PREPARATION OF FOOD PRODUCTS

(75) Inventors: Peggy Garault, Montlhery (FR); Gaëlle Quere, Villebon sur Yvette (FR); Chloé Beal, Paris (FR); Natalia Bomchil, Cachan (FR); Jean-Michel Faurie, Jouy En Josas (FR); Guillaume Gobert, Palaiseau (FR); Gérard Lipowski, Issy les Moulineaux (FR)

(73) Assignee: Compagnie Gervais Danone, Paris (FR)

( * ) Notice: Subject to any disclaimer, the term of this patent is extended or adjusted under 35 U.S.C. 154(b) by 90 days.

(21) Appl. No.: 12/444,347

(22) PCT Filed: Oct. 4, 2007

(86) PCT No.: PCT/EP2007/060572
§ 371 (c)(1),
(2), (4) Date: Apr. 3, 2009

(87) PCT Pub. No.: WO2008/040793
PCT Pub. Date: Apr. 10, 2008

(65) Prior Publication Data
US 2010/0047396 A1    Feb. 25, 2010

(30) Foreign Application Priority Data
Oct. 4, 2006    (FR) ..................................... 06 08690

(51) Int. Cl.
*C12N 1/12*    (2006.01)
*A23L 1/30*    (2006.01)
(52) U.S. Cl. ........................ 435/252.1; 426/72; 426/311

(58) Field of Classification Search ............... 435/252.1; 426/72, 311
See application file for complete search history.

(56) References Cited

FOREIGN PATENT DOCUMENTS

| JP | 62-201592 A | 9/1987 |
|---|---|---|
| JP | 63-91091 A | 4/1988 |
| JP | 63-198993 A | 8/1998 |
| JP | 2000-287676 A | 10/2000 |

OTHER PUBLICATIONS

Tsukamoto, Y. et al., "Construction of a *Bacillus subtilis* (natto) with High Productivity of Vitamin $K_2$ (Menaquinone-7) by Analog Resistance", *Biosc. Biotechnol. Biochem.*, vol. 65 No. 9 2001, pp. 2007-2015.

Gasson, M. J., "Plasmid Complements of *Streptococcus lactis* NCDO 712 and Other Lactic Streptococci After Protoplast-Induced Curing", *Journal of Bacteriology*, vol. 154, No. 1, 1983, pp. 1-9.

Morishita, T., et al., "Production of Menaquinones by Lactic Acid Bacteria", *Journal of Dairy Science*, vol. 82, No. 9, 1999, pp. 1987-1903. XP-000983779.

Vido, K., et al. "Roles of Thioredixon Reductase during the Aerobic Life of *Lactococcus lactis*", *Journal of Bacteriology*, vol. 187, No. 2, Jan. 2005, pp. 601-610. XP-002430548.

Hart, J. P., et al., "Electrochemical Detection of Depressed Circulating Levels of Vitamin $K_1$ in Osteoporosis", *Journal of Clinical Endocrinology and Metabolism*, vol. 60, No. 6, Jan. 1985, pp. 1268-1269.

*Primary Examiner* — Ganapathirama Raghu
(74) *Attorney, Agent, or Firm* — Birch, Stewart, Kolasch & Birch, LLP.

(57) ABSTRACT

The present invention relates to the production of variants of lactic bacteria stems that produce, under standard fermentation conditions, at least about 1.2 times more K2 vitamin than the starting lactic bacteria stems cultured in the same conditions. The invention further relates to a method for preparing food products, including fermented products and/or fresh diary products, enriched with K2 vitamin, and to the food products thus obtained.

5 Claims, No Drawings

METHOD FOR OBTAINING VARIANTS OF LACTIC ACID BACTERIA USABLE FOR PRODUCING VITAMIN K2 AND APPLICATION TO THE PREPARATION OF FOOD PRODUCTS

The present invention relates to the field of food products rich in nutrients, vitamins and/or trace elements in order to improve the content and qualitative and quantitative balance of nutritional intake in humans.

The invention more particularly involves means of enriching food in vitamin K.

More precisely, the present invention concerns obtaining variants of lactic acid bacteria strains that produce, under standard fermentation conditions, at least approximately 1.2 times more vitamin K2 than the initial lactic acid bacteria strains cultured under the same conditions.

The invention also concerns a method for preparing food products, notably fermented products and/or fresh dairy products, enriched in vitamin K2, as well as the food products thus obtained.

Vitamin K is a fat-soluble vitamin that occurs in two natural forms: vitamin K1 (or phylloquinone) and vitamin K2 (or menaquinone)

Vitamin K1 is synthesized by plants. It is principally found in green vegetables (leafy vegetables) and soybean oil. Vitamin K1 is involved more directly in the blood coagulation process.

As for vitamin K2, it is produced by the bacteria of the intestinal flora. It also appears in small quantities in certain foods after a fermentation procedure (cheese, typical Asian products such as Japanese miso and nattō, based on fermented soy, etc.). Numerous bacteria are capable of synthesizing vitamin K2. Thus, in addition to the intestinal flora bacteria, and notably the species *Escherichia coli, Bacillus subtilis* and *Bacteroides* spp., certain species or subspecies of lactic acid bacteria such as *Lactococcus lactis* spp. *lactis, Lactococcus lactis* spp. *cremoris, Leuconostoc lactis, Leuconostoc mesenteroides* and *Propionibacterium* sp. can be mentioned. The quantity of vitamin K2 synthesized by these bacteria generally varies from approximately 29 to 90 μg/L for fermented milk (Morishita et al., 1999). It is important to emphasize that vitamin K2 production is most often measured on freeze-dried cell pellets and the results of these measurements are highly heterogeneous with regard to production levels as a function of the strains tested, which can vary by more than a factor of 3 (Morishita et al., 1999; Parker et al., 2003). In terms of biological activity, vitamin K2 is especially known for its action on soft-tissue calcification.

Vitamin K was initially described for its essential role in the process of blood coagulation. Thus, large deficiencies in vitamin K lead to hemorrhages, with abnormal prolongation of the normal coagulation time, and ecchymoses. For a long time, it was believed that large deficiencies in vitamin K were somewhat rare in adults, and that needs could be met in principle in a satisfactory manner by a varied and balanced diet and by means of endogenous production of the vitamin by colon bacteria. In this regard, the people at risk are typically:

- newborns, whose intestines do not have bacteria producing vitamin K at birth;
- individuals with hepatic, bile or intestinal function disorders (liver diseases, cystic fibrosis, colitis, dysentery, etc.); and
- individuals who take antibiotics for a long time.

More recently, it was discovered that the impact of vitamin K on human health is not limited to its role in blood coagulation mechanisms. In fact, since the 1980s, vitamin K has also been recognized for its role in bone metabolism (Hart et al., 1984; Hart et al., 1985).

This vitamin is a cofactor in an enzymatic reaction modulating the activity of osteocalcin in the regulation of bone formation (Hauschka P V et al., 1989; Ducy P et al., 1996). Its role more precisely consists of modulating the carboxylation of osteocalcin, a key protein that regulates the bone formation process. In the case of vitamin K deficiencies, this reaction does not occur, leading to an increase of the ratio of decarboxylated osteocalcin to carboxylated osteocalcin in the blood (Väänänen et al., 1999).

Demographic developments in the western countries have led to progressive aging of the population, associated in corollary with an increase in degenerative diseases, notably osteoporosis. As a result, osteoporosis is now recognized as a major public health problem.

Demographic estimates made in the 1990s have sounded the alarm by predicting a considerable increase in the incidence of this disease in the next 50 years, notably in seniors. Therefore, it quickly became necessary and urgent to take action to prevent this disease, previously rarely screened for and managed late.

Now it is recognized that prevention of osteoporosis must begin in childhood, through optimal bone growth, and be continued throughout life by maintaining bone mass. It is known that nutritional factors play an important role in the development and maintenance of bone reserves. Up until now, the nutritional strategies envisioned or proposed to prevent osteoporosis relied essentially on two key factors, calcium and vitamin D. However, we now know that other nutritional factors may be worthy of note.

As a result of its major role in bone formation, vitamin K increasingly appears in the literature as a promising route for preserving lifelong bone health in humans.

The recommended dietary intake of vitamin K in humans (1.5 μg/day/kg body weight) was established by considering its role in coagulation phenomena. Now, recent studies suggest that these dietary recommendations are ultimately underestimated if one also takes into account the activity of vitamin K in bone metabolism (Ronden et al., 1998).

Although vitamin K requirements are still poorly understood, it remains that low intakes are associated with a low bone mass and an increased risk of fractures in adults (Hart et al., 1985; Knapen et al., 1989; Szulc et al., 1993; Booth et al, 2000). Moreover, intervention studies in menopausal women have shown that vitamin K reduced bone loss for this target group (Shiraki et al., 2000; Braam et al., 2003). Finally, animal studies suggest that it would play a favorable role during peak bone mass, especially in the case of synergetic combination with vitamin D. However, studies clearly linking vitamin K and bone growth have only been conducted in animals so far.

Moreover, recent studies have introduced additional arguments in favor of the impact of vitamin K on bone metabolism and, in particular, on the constitution and preservation of the bone mass (Booth et al., 2000; Shiraki et al., 2000; Braam et al., 2003; Hirano et Ishi, 2002).

Unlike adults, there are few data available with regard to the beneficial effects of vitamin K on bone metabolism in children. It is only known that it is essential to optimize bone mass during the growth period, in order to build a maximal bone reserve and to protect adults from the risk of future osteoporosis.

In any case, the result of all the data currently available is that improving the vitamin K content in food products is a particularly interesting and promising route for allowing the individual to build and maintain good bone structure.

In this context, there are already industrial products on the food market containing a notable quantity of vitamin K. Certain dairy products containing lactic acid bacteria, such as "Petits Gervais aux Fruits" sold in France by the Applicant can particularly be mentioned. Nevertheless, it is noted that, on the one hand, the vitamin K content of these products generally depends on the type of ferments used and, on the other hand, the *Lactococcus lactis* strains conventionally used in dairy products do not produce a sufficient quantity of vitamin K to truly fill the needs of the population, or even to help alleviate possible vitamin K deficiencies.

Therefore there is a need in the current state of the art for food products, notably fermented products and/or fresh dairy products, that contain vitamin K in sufficient quantities to contribute to satisfying requirements and, if necessary, correcting deficiencies, in children, adolescents, adults and the elderly.

In the following, the terms "vitamin K2" and "vitamin K" are used interchangeably to designate vitamin K2.

The present invention therefore seeks to address this need by proposing the preparation of food products, notably fermented products and/or fresh dairy products, by using new variants of lactic acid bacteria strains that produce quantities of vitamin K significantly greater than those produced by the strain from which they are derived.

Moreover, in the course of their work, the Inventors developed conditions for using lactic acid bacteria that improve the production of vitamin K in a very perceptible manner with regard to the conventional production conditions. Thus, for purposes of preparing food products, such as fermented products and/or fresh dairy products, enriched in vitamin K2, one could advantageously use the vitamin K "overproducer" variants that are the subject of the present invention under the conditions for use identified by the Inventors as particularly favorable to the production of vitamin K that are the subject of French patent application No. 06/08690 of Oct. 4, 2006.

Here, the term "variant" covers:
natural variants, i.e., obtained spontaneously from a reference lactic acid bacteria strain by selection pressure; natural variants that did not undergo any genetic manipulation, but are principally obtained by mutation and selection from the reference strain; and
mutants comprising one or more mutations in their genome, which were induced by genetic engineering, i.e., by directed mutagenesis techniques, particularly by genetic transformation using vectors, applied to the reference strain.

Note that, in certain countries (notably in Europe), precautions must be taken by food producers when they develop products intended for human and/or animal food in which microorganisms are incorporated, especially living microorganisms. Indeed, genetically-modified organisms (microorganisms here) (GMOs or mutants) can cause fear and apprehension in consumers. This negative image of GMOs in certain countries is such that the public has a tendency to boycott foods containing GMOs. Thus, in a context where consumers continually require more transparency regarding the contents of the food products offered to them and the origin of the ingredients that these products contain, producers may be motivated to offer almost exclusively, or even exclusively, products free of GMOs. In the context of the present invention, it could therefore be advantageous that the processed food products containing microorganisms be prepared by using exclusively natural strains or variants of natural strains.

According to a first aspect, the present invention concerns a method for obtaining a natural variant of a lactic acid bacteria producing, under standard fermentation conditions, a greater quantity of vitamin K2, by a factor equal to at least approximately 1.2, than that produced by said lactic acid bacteria strain cultured under the same conditions, said method comprising at least:
a) the culture of said lactic acid bacteria strain under standard fermentation conditions, on a selection medium inducing a modification of the cellular redox state; and
b) the selection of said variant if it produces at least approximately 1.2 times more vitamin K2 than said lactic acid bacteria strain cultured under the same conditions.

The "variants" are, in the sense of the invention, lactic acid bacteria strains capable of producing more vitamin K2 than the strains from which they arise. More precisely, the variants according to the present invention are capable of producing at least approximately 1.2 times more vitamin K2 than the initial strains. Preferably, the quantity of vitamin K2 produced by a variant conforming to the present invention is greater by a factor at least equal to approximately 1.5 than that obtained by culturing the initial lactic acid bacteria strain under the same standard fermentation conditions. It is still more preferred that this factor be equal to at least approximately 1.7, more preferentially equal to at least approximately 1.8, and more preferentially still at least equal to approximately 1.9. Even more preferred values for this factor are at least equal to 2, 2.2, 2.4, 2.5, 2.7, 2.8, 2.9, and 3.

The "reference" or "initial" lactic acid bacteria strains are the strains from which the variants according to the invention are obtained. These strains may be natural or may even be variants themselves, i.e., natural variants or mutants.

Within the scope of the present invention, the "laboratory conditions" are completely standard fermentation conditions well-known to the person skilled in the art. Thus, the expressions "laboratory conditions" and "standard fermentation conditions" are completely synonymous here. The preferred "laboratory conditions" in the sense of the present invention are the following: the strain is precultured on commercial M17 medium (Difco™ M17) or on an equivalent medium. For the subsequent culture, inoculation is done at 1% by the preculture. The incubation temperature is approximately 30° C. The laboratory conditions may be modified if necessary by the person skilled in the art, on the basis of general knowledge and, possibly after routine experimentation. The culture medium is an appropriate medium for culturing lactic acid bacteria strains, notably *Lactococcus* spp. strains.

According to a preferred embodiment, the lactic acid bacteria strain is chosen from among the genera *Lactococcus, Leuconostoc, Enterococcus* and *Propionibacterium*. It is particularly chosen from among the species *Lactococcus lactis, Leuconostoc lactis, Leuconostoc pseudomesenteroides, Leuconostoc mesenteroides, Leuconostoc dextranicum, Enterococcus faecium,* and *Propionibacterium* sp.

Preferably, as is developed below, in the process according to the invention, a selection medium is used chosen from among culture media containing bacitracin or an oxidant such as peroxide.

The selection medium thus used permits inducing a modification in the cell redox state. Advantageously, this modification is correlated to the modification, in said variant and by comparison with the lactic acid bacteria strain from which it arose, of the expression of at least one gene chosen from among genes 1 to 27 listed in Table I below:

TABLE I

| Gene No. | Gene name | Function of the corresponding protein | NCBI accession No. |
|---|---|---|---|
| 1 | cysD | O-acetylhomoserine sulfhydrylase | llmg_0091 |
| 2 | gpo | gpo protein (glutathione peroxidase) | llmg_1088 |
| 3 | metE | 5-methyltetrahydropteroyltriglutamate-homocysteine methyltransferase | llmg_1225 |
| 4 | | putative NADH dehydrogenase | llmg_0195 |
| 5 | metF | MetF Protein methylene tetrahydrofolate reductase | llmg_1226 |
| 6 | trxH | H-type thioredoxin | llmg_0406 |
| 7 | fur | protein for regulation of iron assimilation | llmg_1023 |
| 8 | qor | quinone oxidoreductase | llmg_1850 |
| 9 | frdc | fumarate reductase flavoprotein subunit | llmg_1441 |
| 10 | adhE | alcohol-acetaldehyde dehydrogenase | llmg_2432 |
| 11 | purC | phosphoribosylaminoimidazole-succinocarboxamide synthase | llmg_0973 |
| 12 | cydB | cytochrome d ubiquinol oxidase, subunit II | llmg_1863 |
| 13 | purE | phosphoribosylaminoimidazole carboxylase catalytic subunit | llmg_0999 |
| 14 | purQ | phosphoribosylformylglycinamidine synthase I | llmg_0975 |
| 15 | trxA | Thioredoxin | llmg_0779 |
| 16 | noxB | NADH dehydrogenase | llmg_1734 |
| 17 | cpo | non-heme peroxidase chloride | llmg_1737 |
| 18 | metK | MetF Protein S-adenosylmethionine synthase | llmg_2160 |
| 19 | trxBl | Protein TrxBl thioredoxin reductase | llmg_1588 |
| 20 | cysK | O-acetylserine sulfhydrylase | llmg_1775 |
| 21 | metC | cystathionine beta-lyase | llmg_1776 |
| 22 | metS | MetF Protein Methionyl-tRNA synthetase | llmg_1764 |
| 23 | feoB | ferrous iron transport protein B homolog | llmg_0199 |
| 24 | citB | aconitate hydratase | llmg_0636 |
| 25 | icd | isocitrate dehydrogenase | llmg_0637 |
| 26 | fhuD | ferrichrome ABC transporter substrate binding protein | llmg_0349 |
| 27 | ldh | L-lactate dehydrogenase | llmg_1120 |

Preferably, the expression of genes 1 to 27 is modified in said variant with regard to the lactic acid bacteria strain.

By "modification of the gene expression" is meant here that the gene expression considered is quantitatively modified with regard to that observed in the initial lactic acid bacteria strain:
either the expression is increased, and this will preferably be the case for at least one gene chosen from 1 to 15;
or the expression is decreased, and this will preferably be the case for at least one gene chosen from 16 to 27.

Preferably, the variant is selected from step b) if it produces, under standard fermentation conditions:
at least approximately 1.5 times more, preferably at least approximately 2 times more, even more preferably at least approximately 3 times more vitamin K than ferment CHN-12; and/or
at least approximately 1.5 times more, preferably at least approximately 2 times more, even more preferably at least approximately 3 times more and advantageously up to approximately 10 times more vitamin K2 than model natural strain MG1363.

Advantageously, the variant is selected in step b) if it produces, under standard fermentation conditions, at least approximately 5.5 μg of vitamin K2 per 100 g of fermented milk.

If the quantity of vitamin K2 produced by the variants is at least approximately 5.5 μg per 100 g of fermented milk under standard experimental conditions, it can be called a vitamin K2 "overproducer" variant. In particular, a variant in the sense of the present invention produces at least approximately 5.7 μg, still more preferably at least approximately 5.9 μg, and even more preferably at least approximately 6.1 μg and, better still, at least approximately 6.3 μg of vitamin K2 per 100 g of fermented milk under standard fermentation conditions. More preferably, a variant according to the present invention produces at least approximately 6.5 μg, preferably at least approximately 7 μg, preferably still at least approximately 7.5 μg, still more preferably at least approximately 8 μg, even more preferably 8.5 μg, even more preferably still at least approximately 9 μg and even better, at least approximately 9.5 μg, and better still, at least approximately 10 μg of vitamin K2 per 100 g of fermented milk under standard fermentation conditions.

In a second aspect, the present invention concerns a natural variant of a lactic acid bacteria strain that can be obtained by a process such as described above, as well as biologically pure cultures and fractions of cultures of said variant, said variant producing, under standard fermentation conditions, a quantity of vitamin K2 greater by a factor at least equal to approximately 1.2 than that produced by the initial lactic acid bacteria strain cultured under the same conditions.

In particular, a variant conforming to the present invention produces, under laboratory conditions (or standard fermentation conditions):
at least approximately 1.5 times more, preferably at least approximately 2 times more, preferably still at least approximately 3 times more, vitamin K2 than the CHN-12 ferment sold by CHR. Hansen A/S (Horsholm, D K); and/or
at least approximately 1.5 times more, preferably at least approximately 2 times more, still more preferably approximately 3 times more and, advantageously, up to at least approximately 10 times more, vitamin K2 than the model natural strain *Lactococcus lactis* ssp. *cremoris* MG1363 filed with CBS (Baarn, N L) under number CBS 364.89. This model strain of *Lactococcus lactis* ssp. *cremoris* is perfectly well-known to the person skilled in the art. It was described for the first time by Gasson in 1983 (Gasson M., 1983).

In agreement with the definition of "natural variant" given above, a variant according to the present invention is a natural variant obtained by selection pressure on an appropriate culture medium.

Several examples of such natural variants obtained by selection pressure are provided in the present application. Briefly (for more detail, see the "Examples" part below), the preferred examples of natural variants and methods for obtaining them are the following.

According to a first embodiment, a natural variant conforming to the invention is obtained by selection pressure in a culture medium containing bacitracin. As a function of the initial strains, the concentration of bacitracin in the medium can be, for example, at least approximately 0.4 mg/L, preferably at least approximately 1 mg/L, still more preferably at least approximately 2 mg/L, and even more preferred at least approximately 3 mg/L and in the most preferred manner of all, at least approximately 4 mg/L. However, it is clear for the person skilled in the art that the concentration of bacitracin to be used to obtain natural variants conforming to the invention will be determined as a function of the level of bacitracin resistance of the lactic acid bacteria strain used initially. If necessary, the person skilled in the art will work with several different concentrations chosen as a function of the properties of the initial strain. Advantageously, the person skilled in the art could work with bacitracin concentration ranges.

A particularly interesting natural variant essentially has the same biological properties as natural variant I-3557, filed with the Collection Nationale de Culture des Microorganismes [National Microorganism Culture Collection] (CNCM, Institut Pasteur, 25, rue du Docteur Roux, 75724 Paris Cedex 15, France) on Jan. 20, 2006.

By the expression "a variant A having essentially the same biological properties as natural variant I-3557", is meant here that variant A is a natural variant obtained by selection pressure in a medium containing bacitracin. However, the concentration of bacitracin used in the medium to obtain variant A is not determinant for satisfying the present definition. The determinant condition, in return, is that variant A is capable of producing, under laboratory conditions, approximately as much, preferably at least as much, vitamin K2 as variant I-3557. A natural variant in the sense of the invention is preferably natural variant I-3557.

In a second embodiment, a natural variant according to the present invention is obtained by selection pressure on a culture medium containing at least one oxidant. For example, the oxidant can be chosen from among peroxide, perchloric ions, ferrous ions, menadione, paraquat, oxygen or any other appropriate oxidant compound. Preferably, the oxidant is peroxide. Like with bacitracin, the peroxide concentration in the medium is determined as a function of the initial lactic acid bacterial strain. For example, one or more concentrations of peroxide in the following ranges can be tested: at least approximately 20, 25, 27, 28.5 mg/L. Once again, the person skilled in the art will determine one or more concentrations, or even a range of concentrations, appropriate for peroxide that will be tested experimentally in the usual way.

Advantageously, a natural variant conforming to the invention essentially has the same biological properties as natural variant I-3558 (filed with the CNCM on Jan. 20, 2006). The definition of the expression "a variant A having essentially the same biological properties as natural variant I-3557" given above is applied here mutatis mutandis (peroxide instead of bacitracin; variant I-3558 instead of variant I-3557). Preferably, such a variant is natural variant I-3558.

A third aspect of the present invention pertains to the use of particular selection conditions to obtain natural variants of lactic bacteria strains that, conforming to the preceding description, produce, under standard fermentation conditions, at least approximately 1.2 times more vitamin K2 than the initial strains cultured under the same conditions.

These are notably:

the use of bacitracin resistance; and/or the use of resistance to an oxidant, such as peroxide.

As indicated previously, said natural variants are advantageously capable of producing at least approximately 5.5 µg of vitamin K2 per 100 g of fermented milk under standard fermentation conditions.

A fourth aspect of the present invention pertains to a lactic ferment that comprises at least one variant such as described above.

According to a fifth aspect, the present invention concerns a production method for a food product enriched in vitamin K2, comprising at least:

a) the use of at least one variant and/or at least one ferment such as described above, in an intermediate preparation of said product; and b) obtaining said product enriched in vitamin K2.

Alternatively, a process for increasing the vitamin K2 content of a food product comprises at least:

a) the use of at least one variant and/or at least one ferment such as described above, in an intermediate preparation of said product; and b) obtaining said product enriched in vitamin K2.

The variants and/or the lactic ferment can notably be implemented by using bacteria concentrates precultured in place (on the food product production site), or by using bacteria precultured by a ferment supplier, then packaged and sent to the food production site or sites. The suppliers may package the bacteria in the fresh or frozen state; alternatively, the bacteria may be dried or freeze-dried. The bacteria are, in all cases, added to the dairy product mass in a completely conventional manner (like any other known lactic ferment).

A sixth aspect of the present invention pertains to a food product enriched in vitamin K2 that can be obtained by a process such as disclosed above. The invention pertains to human and/or animal food products, with an emphasis on human food products. Advantageously, such a food product enriched in vitamin K2 strengthens the bone solidity of the person who consumes it. Preferably, this person is a child.

Preferably, a food product in the sense of the invention is chosen from among fermented products, fresh fermented or unfermented dairy products, products based on fermented or unfermented plant juices (fruits, vegetables, grains, soy, etc.), and their combinations. In a more particularly preferred manner, a food product in the sense of the invention is a fermented product and/or a fresh dairy product.

In the context of the invention, "fresh dairy products" designates more particularly fresh and fermented dairy products, ready for human consumption, i.e., fresh and fermented dairy foods. The present application particularly pertains to fermented milk and yoghurt. Said fresh and fermented dairy foods can alternatively be fromage blanc or petit-suisse.

The terms "fermented milk" and "yoghurt" are given their usual meanings in the dairy industry, i.e., products that are intended for human consumption and that arise from lactic acid fermentation of a dairy substrate. These products may contain secondary ingredients such as fruits, vegetables, sugar, etc. For example, refer to French Decree 88-1203 of Dec. 30, 1988 relating to fermented milk and yoghurt, published in the *Journal Officiel de la République Française on Dec.* 31, 1988.

One can also refer to the "Codex Alimentarius" (prepared by the Codex Alimentarius Commission of the FAO and WHO, and published by the Information Division of the FAO; see more particularly volume 12 of the Codex Alimentarius "Codex Standards for milk and dairy products" and standard "CODEX STAN A-1 1 (a)-1975").

The expression "fermented milk" is thus reserved in the present application for dairy products prepared from a dairy substrate that has undergone a treatment at least equal to pasteurization, and then inoculated with microorganisms belonging to one or more characteristic species for each product. A "fermented milk" has not undergone any treatment removing a constitutive element of the dairy substrate used, and particularly has not had the coagulum drained. The coagulation of "fermented milk" must not be obtained by means other than those that result from the activity of the microorganisms used.

The term "yoghurt" is reserved for fermented milk obtained, according to local and established usage, by the development of specific thermophilic lactic acid bacteria called *Lactobacillus bulgaricus* and *Streptococcus thermophilus*, which must be alive in the final product, in an amount of at least 10 million bacteria per gram of the lacteous portion.

In certain countries, regulations allow the addition of other lactic acid bacteria in the production of yoghurt, and notably the additional use of strains of *Bifidobacterium* and/or *Lactobacillus acidophilus* and/or *Lactobacillus casei*. These additional lactic acid strains are intended to confer various properties to the final product, such as improving the balance of intestinal flora or modulating the immune system.

In practice, the expression "fermented milk" is thus generally used to designate fermented milk other than yoghurt. Fermented milk products can have various names, according to the country, such as, for example "Kefir", "Kumis", "Lassi", "Dahi", "Leben", "Filmj8lk", "VIIIi", and "Acidophilus milk".

In the case of fermented milk, the quantity of free lactic acid contained in the fermented dairy substrate must not be less than 0.6 g per 100 g at the time of sale to the consumer, and the content of protein with regard to the lacteous portion should not be less than that of regular milk.

Finally, the name "fromage blanc" or "petit-suisse" is, in the present application, reserved for an unaged, unsalted cheese, that has been fermented by only lactic acid bacteria (and no fermentation other than lactic acid fermentation). The content in dry solids of fromage blanc can be lowered to 15 g or 10 g per 100 g of fromage blanc, according to whether their fat content is greater than 20 g or at most 20 g per 100 g of fromage blanc, after complete desiccation. The dry solids content of a fromage blanc is comprised between 13 and 20%. The dry solids content of a petit-suisse is not less than 23 g per 100 g of petit-suisse. It is generally comprised between 25 and 30%. Fromage blanc and petit-suisse are generally grouped under the name "fresh cheeses", used conventionally in the technical field of the present invention.

In a seventh aspect, the present invention concerns the use of at least one variant and/or at least one ferment as described above, to prepare a food product enriched in vitamin K2.

Advantageously, such a food product enriched in vitamin K2 strengthens the bone solidity of the person who consumes it. Preferably, this person is a child.

It is clear that the present invention is not limited by the single description above. Other embodiments and advantages of the invention will arise upon reading the examples below, provided purely for purposes of illustration.

EXAMPLES

As a preliminary remark, it should be noted that the protocols for obtaining the natural variants described below are applicable to any initial lactic acid bacteria strain. For practical reasons, as a function of the initial strain, the person skilled in the art may be induced to modify certain experimental conditions developed by the Inventors. In any case, the modifications that the person skilled in the art may introduce to the procedures below will be minor and require only simple routine operations not involving any inventive step.

I—Obtaining and Using Natural Variants Resistant to Bacitracin

Although exposure to agents such as bacitracin or peroxide is known to permit selecting bacteria strains that have an increased resistance to these agents, the link between bacitracin or peroxide resistance and bacterial vitamin K2 production levels has never been established in the literature.

Within the scope of their work, the Inventors discovered in a completely unexpected manner that bacteria were capable of developing an original mechanism for resistance to certain agents such as bacitracin or peroxide involving an increase of vitamin K2 production. The Inventors envisioned benefiting from this discovery for purposes of obtaining natural variants of lactic acid bacteria (notably *Lactococcus* lactis) that can overproduce vitamin K2 by using bacitracin or peroxide as selection agents.

I-1 Protocol for Obtaining Variants Resistant to Bacitracin

A preculture is made from a crystal of a natural strain of *Lactococcus lactis* in the presence of 2 mL conventional commercial M17 culture medium (M17 medium, Difco™) with the addition of 5 g/L lactose (hereinafter M17 Lac medium) and hemin (20 μL/mL) (hereinafter, M17 Lac+ hemin medium). Incubation was performed with stirring at 30° C.

The preculture served to inoculate 2 mL of M17 Lac+ hemin supplemented with bacitracin (4 μg/mL). The degree of inoculation was 1%. The culture was then incubated for 48 h at 30° C. with stirring.

Then, 100 μL of this suspension were deposited on an M17 Lac agar. A paper disk soaked with 2.5 mg bacitracin was deposited in the center of the dish. The agar was incubated for 48 h at 30° C. The clones near the paper disk were cultured in the presence of bacitracin (4 μg/mL) in 2 mL M17 Lac+ hemin. The incubation lasted 24 h at 30° C. with stirring.

The cells were isolated on M17 Lac agar in the presence of bacitracin (2 μg/mL) after an incubation of 48 h at 30° C. The isolated clones were cultured on M17 Lac+hemin, and then incubated for 24 h at 30° C. with stirring. This suspension served for creating the frozen stock.

These experiments permitted the Inventors to select the natural variant *Lactococcus* lactis subsp. *cremoris* I-3557 filed with CNCM on Jan. 20, 2006.

I-2 Protocol for Making a Dairy Product Example with the "Bacitracin" Variant

A preculture was done from a crystal of the strain in 2 mL M17 Lac.

The preculture served to inoculate 50 mL UHT whole milk at 1%, which was incubated at 30° C. for 24 h.

Table II below gives the results of the vitamin K2 assay expressed in μg Equivalent MK-4/100 g of product, for the bacitracin resistant variant and the corresponding wild-type strain.

TABLE II

| Strain | I-3557 | Wild-type |
|---|---|---|
| Vitamin K (in μg/100 g) | 8.90 | 3.32 |

The bacitracin-resistant variant overproduces vitamin K by a factor of 3 compared with the initial wild-type strain.

II—Obtaining and Using Natural Variants Resistant to Peroxide

*Lactococcus* lactis respiration was discovered fairly recently (Duwat et al., 2001). Sequencing the genome of a strain of *L. lactis* (IL1403) confirmed the presence of genes coding for the functions necessary to aerobic respiration (Bolotin et al., 2001). In fact, *L. lactis* has the men and cytABCD operons coding for the proteins necessary to menaquinone synthesis and biogenesis of cytochrome D. This species also has three genes involved in the last steps of heme synthesis (hemH, hemK and hemN, which are required in the oxidation of porphyrin for attaching the iron to the heme), but does not have the genes involved in the first steps of this process. However, *L. lactis* can perform oxidative phosphorylation in the presence of protoporphyrinogen.

It was also shown that *L. lactis* could respire in the presence of oxygen and heme in the culture medium. This respiration permitted the cells to reach a larger biomass and the final pH observed is higher than what is usually obtained. Cultures in the presence of oxygen and/or heme permit obtaining comparable growth curves during approximately the first 6 or 7 hours of fermentation. Then, the consumption of glucose decreases in the case of cultures in the presence of oxygen and heme, and the production of lactate is thus reduced. This translates a metabolic shift which occurs late in the culture. *L. lactis* respiration therefore occurs toward the end of the exponential growth phase (Duwat et al., 2001).

The role of *L. lactis* respiration is not yet known, nor is the role of the vitamin K2 in this type of fermentative metabolism. The Inventors further observed that vitamin K2 was produced by *L. Lactis* strains while respiration was not yet induced under the conditions tested (no heme in the medium and no stirring permitting good oxygenation of the medium).

In the cytoplasm, the proteins had few disulfide bridges, unlike the extracellular proteins. There is a widespread enzymatic system that allows limiting the number of disulfide bridges. The S—S bonds are reduced into SH functions by means of an enzyme, thioredoxin. This enzyme is regenerated by thioredoxin reductase. Vido et al (2005) created an *L. lactis* mutant trxB1 by genetic engineering. The trxB1 gene codes for thioredoxin reductase. Two-dimensional electrophoresis study of the proteins synthesized by this mutant showed that it overproduced certain enzymes of the vitamin K2 synthesis pathway, i.e., the MenB and MenD enzymes.

In view of these data and after personal observations, the Inventors believed that one of the possible routes for improving the production of vitamin K2 by *L. lactis* could be to induce respiration. Another route could be to try to mobilize vitamin K2 to respond to oxidative stress.

The Inventors therefore sought to obtain natural variants resistant to oxidative stress. It is important to note that the natural variants obtained do not show overexpression of the Men operon.

I-11 Protocol for Obtaining Variants Resistant to Oxidative Stress

Peroxide was chosen as an example of a usable oxidant. Of course, other oxidants such as perchloric ions, ferrous ions, menadione, paraquat, oxygen or any other appropriate oxidant compound could be used under similar conditions.

After a preculture on M17 Lac medium, the initial natural strains were transplanted into the medium containing increasing concentrations of peroxide (for example, a range from at least 20 to at least approximately 25, 27, 28.5 mg/L). Cultures were incubated at 30° C. After 24 h, since the first tubes of the concentration range did not show any growth, they were returned to incubate for an additional 24 h. The clones were then isolated by streaking on agar medium. A clone was selected for a peroxide concentration of 27 mg/L. The Inventors noted that beyond a peroxide concentration of 28.5 mg/L, there was no growth.

These experiments permitted the Inventors to select the natural variant *Lactococcus lactis* subsp. *cremoris* I-3558 filed with CNCM on Jan. 20, 2006.

II-2 Protocol for Making a Dairy Product Example with the "Peroxide" Variant

The selected clone was grown in whole milk for 24 h. Samples were then taken and frozen at −80° C. for a final vitamin K assay.

Table III below indicates the quantity of vitamin K2 produced by the peroxide-resistant variant, compared to the quantity produced by the initial strain (quantities expressed in µg Equivalent MK-4/100 g of fermented milk).

TABLE III

| Strain | Vitamin K (µg/100 g) |
|---|---|
| Wild-type | 2.92 ± 0.45 |
| I-3558 | 5.94 ± 0.76 |

As shown in Table III above, the variant produces approximately twice as much vitamin K2 as the corresponding wild-type strain.

III—Genotype Characterization of Natural Variants I-3557 and I-3558.

III-1-Materials and Methods

The strains were cultured for one night at 30° C. on M17 lactose medium. A commercial whole milk was inoculated by means of each of these strains in an amount of 1% preculture. The inoculated milk was placed in 12 mL tubes. The fermentations were stopped in the desired physiological state, the exponential growth phase or the slowing phase, by plunging the tubes into liquid nitrogen. The tubes were then stored at −80° C. until used. The preceding experiments showed that vitamin K is essentially produced in the slowing phase (data not shown).

Extraction of Total RNA

All the samples were treated identically.

These samples were thawed in the presence of RNA protect (Qiagen—ref 76506) in order to prevent degradation of the RNA. The cells from these samples were recovered by centrifugation.

Then, the cellular RNA of each sample was isolated by means of a Mixer Mill MM 300 cell disrupter (Qiagen) with beads (Biospec Products—ref 11079101z, Zirconia/Silica Beads diameter 0.1 mm) in the presence of Trizol® (Invitrogen—ref 15596-026). The concentration and the purity ratios (230/260 and 260/280 nm) of the RNA were then measured by spectrophotometry with the ND-1000 Nanodrop® spectrophotometer (Nanodrop Technologies). The RNA quality (RIN, ratio 16/23 S) was also measured by means of the 2100 Bioanalyzer—expert software, version B.02.05 (Agilent Technologies) and RNA 6000 Series II Nano Kits (Agilent Technologies—ref 5067-1511).

Labeling of mRNA and Hybridization on DNA Chip

The targets were synthesized by reverse transcription of mRNA using the same specific reverse primers as those used for the synthesis of the PCR products spotted onto the DNA chips. These direct markers were made by the Eurogentec company by means of the CyScribe first strand cDNA labeling System dCTP/purification CyScribe GFX kit (Amersham—ref RPN6202X) and fluorescent molecules Cy3-dCTP/Cy5-dCTP bound to the nucleotides (Perkin Elmer—ref NEL576/NEL577).

The hybridization of the labeled targets on the DNA chip to the PCR products, of the *Lactococcus lactis cremoris* MG1363 strain (sequence available on NCBI), was done by the Eurogentec company, who produces and sells these DNA chips itself. This company uses a conventional hybridization and washing protocol (Eurogentec hybridization buffer—ref AR-HYB-01, incubation for one night at 42° C. in the Advalytix Slidebooster SB800 station—Implen, washing of the hybridized DNA chips in a 0.2×SSC/0.1% SDS buffer for 5 minutes with stirring at ambient temperature then rinsing in a 0.2×SSC buffer for 5 minutes at ambient temperature with occasional stirring then drying of the DNA chips by centrifugation at 1000 rpm for 5 minutes).

The hybridization data were acquired by the Eurogentec company by means of an Axon 4100A scanner and GenePix Pro 5.1 software (Axon Instruments). The hybridized DNA scans were then sent to the Inventors by the Eurogentec company.

Data Processing

The digital results from scanning the hybridized DNA chips were obtained by the Inventors by means of GenePix Pro 6.0 software.

These preliminary digital results were followed by statistical processing with MANGO software developed by the Transcriptomique GODMAP platform of the CNRS of Gif sur Yvette (91) so as to obtain significant expression ratios; each spot corresponding to a gene was duplicated on the DNA chips and each biological experiment was reproduced three times, including a label swap (dye-swap) in order to limit the biases inherent in incorporating fluorescent molecules bound to nucleotides, thus representing six slides for comparison.

The differential expression ratios were selected on the basis of reproducibility criteria such as the adjusted p-value ($<0.01$), with regard to the mean background noise and on the value of the expression ratios ($r \geq 2.00$ and $r \leq 2.00$).

III-2—Results

The two variants had similar results with regard to the expression of certain genes. The majority of genes concerned involved the redox state of the cell and notably in relation to the Fe—S clusters. In this context, methionine and cysteine metabolism are modified, as is iron transport. The expression of several enzymes involved in oxidative stress defense mechanisms was modified: thioredoxin H, thioredoxin B1, NADH dehydrogenase, NADH dehydrogenases, glutathione peroxidase, etc.

In the exponential phase, certain enzymes involved in *L. Lactis* respiration are overexpressed: fumarate reductase (frdC) and cytochrome oxidase (cydD). Likewise, purine base metabolism appears to be modified.

Table IV below gives the expression ratios of certain genes and establishes a comparison between the variants and the wild-type strain in the slowing phase.

TABLE IV

| Protein | Gene | Gene number in the present application | NCBI accession No. | Variant I-3557 | Variant I-3558 |
|---|---|---|---|---|---|
| O-acetylhomoserine sulfhydrylase | cysD | 1 | IImg_0091 | 4.04 | 3.70 |
| gpo protein (glutathione peroxidase) | gpo | 2 | IImg_1088 | 3.16 | 3.73 |
| 5-methyltetrahydropteroyltri-glutamate homocysteine methyltransferase | metE | 3 | IImg_1225 | 2.94 | 3.12 |
| Putative NADH dehydrogenase | — | 4 | IImg_0195 | 2.66 | 3.77 |
| MetF protein methylene tetrahydrofolate reductase | metF | 5 | IImg_1226 | 2.44 | 2.64 |
| thioredoxin H-type | trxH | 6 | IImg_0406 | 2.37 | 2.63 |
| ferric uptake regulation protein | fur | 7 | IImg_1023 | 2.16 | 4.91 |
| quinone oxidoreductase | qor | 8 | IImg_1850 | 2.13 | 2.35 |
| NADH dehydrogenase | noxB | 16 | IImg_1734 | −2.01 | −2.42 |
| non-heme chloride peroxidase | cpo | 17 | IImg_1737 | −2.39 | −2.52 |
| MetK protein S-adenosylmethionine synthase | metK | 18 | IImg_2160 | −3.51 | −2.07 |
| TrxB1 protein thioredoxin reductase | trxB1 | 19 | IImg_1588 | −3.62 | −2.94 |
| 0-acetylserine sulfhydrylase | cysK | 20 | IImg_1775 | −3.86 | −3.54 |
| cystathionine beta-lyase | metC | 21 | IImg_1776 | −5.02 | −5.27 |
| L-lactate dehydrogenase | ldh | 27 | IImg_1120 | −10.98 | −4.31 |

Table V below gives the expression ratios of genes in the variants by comparison with the wild-type strain in the exponential growth phase.

TABLE V

| Protein | Gene | Gene number in the present application | NCBI accession No. | Variant I-3557 | Variant I-3558 |
|---|---|---|---|---|---|
| fumarate reductase flavoprotein subunit | frdC | 9 | IImg_1441 | 6.28 | 6.52 |
| alcohol-acetaldehyde dehydrogenase | adhE | 10 | IImg_1916 | 4.36 | 3.14 |
| phosphoribosylaminoimidazole-succinocarboxainide synthase | purC | 11 | IImg_0973 | 3.61 | 3.13 |
| cytochrome d ubiquinol oxidase, subunit 11 | cydB | 12 | IImg_1863 | 3.15 | 2.95 |
| phosphoribosylaminoimidazole carboxylase catalytic subunit | purE | 13 | IImg_0999 | 2.12 | 2.58 |
| phosphoribosylformylglycinamidine synthase I | purQ | 14 | IImg_0975 | 2.29 | 2.42 |
| Thioredoxin | trxA | 15 | IImg_0779 | 3.07 | 2.19 |
| putative NADH dehydrogenase | — | 4 | IImg_0195 | 2.41 | 2.02 |

TABLE V-continued

| Protein | Gene | Gene number in the present application | NCBI accession No. | Variant I-3557 | Variant I-3558 |
|---|---|---|---|---|---|
| MetS protein Methionyl-tRNA synthetase | metS | 22 | IImg_1764 | −2.49 | −2.08 |
| ferrous iron transport protein B homolog | feoB | 23 | IImg_0199 | −3.42 | −2.21 |
| TrxBl protein thioredoxin reductase | trxB1 | 19 | IImg_1588 | −2.74 | −2.58 |
| aconitate hydratase | citB | 24 | IImg_0636 | −3.1 | −2.88 |
| isocitrate dehydrogenase | icd | 25 | IImg_0637 | −7.32 | −7.16 |
| ferrichrome ABC transporter substrate binding protein | fhuD | 26 | IImg_0349 | −15.1 | −16.80 |

REFERENCES

Bolotin et al. 2001. Genome Research 11, 731-753
Duwat et al. 2001. J. Bacteriol. 183(15), 4509-16
Morishita et al. 1999. J. Dairy Sci. 82, 1897-1903
Parker et al. 2003. Journal of Food Science 68(7), 2325-2330
Vido et al. 2005. J. Bact. 187, 601-10
Gasson M. 1983. J. Bact. 154, 1-9
Hart J P, et al. [letter]. Lancet. 1948; 2:283
Hart J P, et al. J. Clin Endocrinol Metab. 1985; 60:1268-9
Hauschka P V et al. Physiol Rev. 1989; 69:990-1047
Ducy P, et al. Nature. 1996; 382:448-52
Väänänen H K, et al. Calcif Tissue Int. 1999; 64:S79
Ronden J E, et al. Biochim Biophys Acta. 1998; 1379:16-22
Knapen M H, et al. Ann Intern Med. 1989 Dec. 15; 111(12): 1001-5
Szulc P, et al. J Clin Invest. 1993 April; 91(4):1769-74
Booth S L, et al. Am J Clin Nutr. 2000; 71:1201-8
Shiraki M, et al. J Bone Miner Res. 2000; 15:515-21
Braam L A J L M, et al. Calcif Tissue Int. 2003 July; 73(1): 21-6
Hirano J and Ishii Y. J Orthop Sci. 2002; 7:364-369
Tsukamoto Y, et al. Biosci. Biotechnol. Biochem. 2001; 65(9):2007-2015
Cocaign-Bousquet, M., et al. Journal of Applied Bacteriology 1995; 79, 108-116

The invention claimed is:

1. A natural variant of a lactic acid strain, wherein it is natural variant I-3557 filed with the Collection Nationale de Culture des Microorganismes (CNCM, Institut Pasteur, 25, rue du Docteur Roux, 75724 Paris Cedex 15, France) on Jan. 20, 2006.

2. A natural variant of a lactic acid strain, wherein it is natural variant I-3558 filed with the Collection Nationale de Culture des Microorganismes (CNCM, Institut Pasteur, 25, rue du Docteur Roux, 75724 Paris Cedex 15, France) on Jan. 20, 2006.

3. A method for producing a food product enriched in vitamin K2, comprising at least:
   a) the use of at least one variant according to claim 1 or 2; and
   b) obtaining said product enriched in vitamin K2.

4. A lactic ferment comprising at least one variant according to claim 1.

5. A lactic ferment comprising at least one variant according to claim 2.

* * * * *